(12) United States Patent
Buczynski et al.

(10) Patent No.: US 8,206,660 B2
(45) Date of Patent: Jun. 26, 2012

(54) DOOR SEAL SYSTEM FOR STEAM STERILIZER

(75) Inventors: Peter J. Buczynski, Girard, PA (US); James M. Huber, Girard, PA (US); David A. Karle, Girard, PA (US); Teppo Nurminen, Ojakkala (FI); David F. McCall, Edinboro, PA (US)

(73) Assignee: American Sterilizer Company, Mentor, OH (US)

( * ) Notice: Subject to any disclaimer, the term of this patent is extended or adjusted under 35 U.S.C. 154(b) by 394 days.

(21) Appl. No.: 12/414,176

(22) Filed: Mar. 30, 2009

(65) Prior Publication Data

US 2010/0247388 A1 Sep. 30, 2010

(51) Int. Cl.
*A61L 2/00* (2006.01)
*E06B 7/18* (2006.01)
(52) U.S. Cl. ....................................... 422/296; 49/477.1
(58) Field of Classification Search .................. 422/296; 49/477.1
See application file for complete search history.

(56) References Cited

U.S. PATENT DOCUMENTS

| | | | | |
|---|---|---|---|---|
| 4,228,135 A | | 10/1980 | Wolff | 422/296 |
| 4,335,075 A | * | 6/1982 | Kackos | 422/112 |
| 4,999,165 A | * | 3/1991 | Calabra et al. | 422/113 |
| 6,319,479 B1 | * | 11/2001 | Houston | 422/292 |
| 6,698,439 B2 | * | 3/2004 | Kamikawa et al. | 134/138 |
| 6,984,359 B2 | | 1/2006 | Florkey et al. | 422/3 |

* cited by examiner

*Primary Examiner* — Kevin Joyner
(74) *Attorney, Agent, or Firm* — Kusner & Jaffe; Michael A. Centanni

(57) ABSTRACT

The present invention provides a sterilizer having a housing defining a sterilization chamber. An opening in the housing communicates with the chamber. A surface surrounds the opening, and a door is movable between one of an open position allowing access to the chamber through the opening and a closed position covering the opening. A seal element is associated with the surface for forming a fluid-tight seal between the door and the surface when the door is in the closed position. An operating system is provided for applying pressure to one side of the seal from a first source external to the operating system to force the seal into engagement with the door. Sensing means are provided for monitoring the pressure applied to the seal from the first pressure source. A second source of pressure is provided in the operating system and is connectable to the seal. Valve means connect the pressure source to the steam system if the sensing means detects a pressure below a set pressure sufficient to sustain a seal between the door and the surface.

6 Claims, 7 Drawing Sheets

DOOR SEAL SYSTEM FOR STEAM STERILIZER

FIELD OF THE INVENTION

The present invention relates generally to sterilizers and, more particularly, to a system for sealing doors on a steam sterilizer.

BACKGROUND OF THE INVENTION

Steam sterilizers are well known and widely used in hospitals, laboratories, and other facilities for sterilizing and decontaminating many types of articles. For steam sterilizers installed in high-level containment facilities that work with agents that are potentially life threatening, it is important that the doors on the sterilizer be kept sealed in the event of a utility failure, so as to prevent contaminants in the chamber from being released.

In the past, a "passive" or "crush" seal arrangement has been the accepted standard for steam sterilizer door seals. A passive seal is made by mechanically applying a force to the door to force the door into engagement with the sterilizer chamber. Typically, the mechanical force is applied by a manually operated screw mechanism that keeps the door sealed against the sterilizer chamber. A passive seal may pass a vacuum leak test as a result of the chamber door being pulled tightly against a seal by the vacuum, which forces the door into the end frame of the sterilizer. However, once the chamber is pressurized, the door is forced away from the end frame of the sterilizer, which may result in a potential leak around the seal.

Because of the foregoing problem, and because of the cost and complexity of most manually operated mechanical seals, sterilizer technology has moved away from traditional passive seals to "active seals," wherein an external pressure force, typically steam or air, is used to apply a pressure to accomplish sealing. A problem with active seals is that the seal around the door may be compromised if the external pressure force is lost.

The present invention provides a system for creating an active seal around a door on a steam sterilizer, which system is capable of maintaining a seal for a predetermined period of time even if all customer-supplied utilities to the system are lost.

SUMMARY OF THE INVENTION

In accordance with a preferred embodiment of the present invention, there is provided a sterilizer having a housing defining a sterilization chamber. An opening in the housing communicates with the chamber. A surface surrounds the opening, and a door is movable between one of an open position allowing access to the chamber through the opening and a closed position covering the opening. A seal element is associated with the surface for forming a fluid-tight seal between the door and the surface when the door is in the closed position. An operating system is provided for applying pressure to one side of the seal from a first source external to the operating system to force the seal into engagement with the door. Sensing means are provided for monitoring the pressure applied to the seal from the first pressure source. A second source of pressure is provided in the operating system and is connectable to the seal. Valve means connect the pressure source to the steam system if the sensing means detects a pressure below a set pressure sufficient to sustain a seal between the door and the surface.

An advantage of the present invention is a door-seal system for creating an active seal around a door of a steam sterilizer.

Another advantage of the present invention is a door-seal system as described above that establishes an external pressure force to seal the door of a steam sterilizer.

Another advantage of the present invention is a door-seal system as described above for use in a high-level contamination facility.

Another advantage of the present invention is a door-seal system as described above that includes a back-up pressure source to maintain a pressure force against a seal element for a predetermined period of time, following loss of customer-supplied utilities to the sterilizer.

Another advantage of the present invention is a door-seal system as described above that includes sensors and controls that insure that the seal around a door on a steam sterilizer will remain sealed under a large variety of failure conditions.

Another advantage of the present invention is a door-seal system as described above that constantly monitors itself for failures and malfunctions.

Another advantage of the present invention is a door-seal system as described above that includes a door seal designed to allow pressure from within the sterilizer chamber to flow into a seal groove during a loss of utilities, such that the door seal will remain activated as long as a positive pressure remains within the sterilizer chamber.

A still further advantage of the present invention is a door-seal system as described above that monitors the system and seal so as to detect leaks at the beginning of a cycle, thereby allowing a system user to abort the sterilization cycle.

A still further advantage of the present invention is a door-seal system as described above, having the ability to keep the sterilizer door sealed even if all utilities have been lost.

A still further advantage of the present invention is a door-seal system as described above that has the ability to keep the sterilizer door sealed even in the event of a system malfunction.

A still further advantage of the present invention is a door-seal system as described above, having the ability to detect a door seal that is leaking from the seal to the sterilizer chamber or from the seal to the atmosphere.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
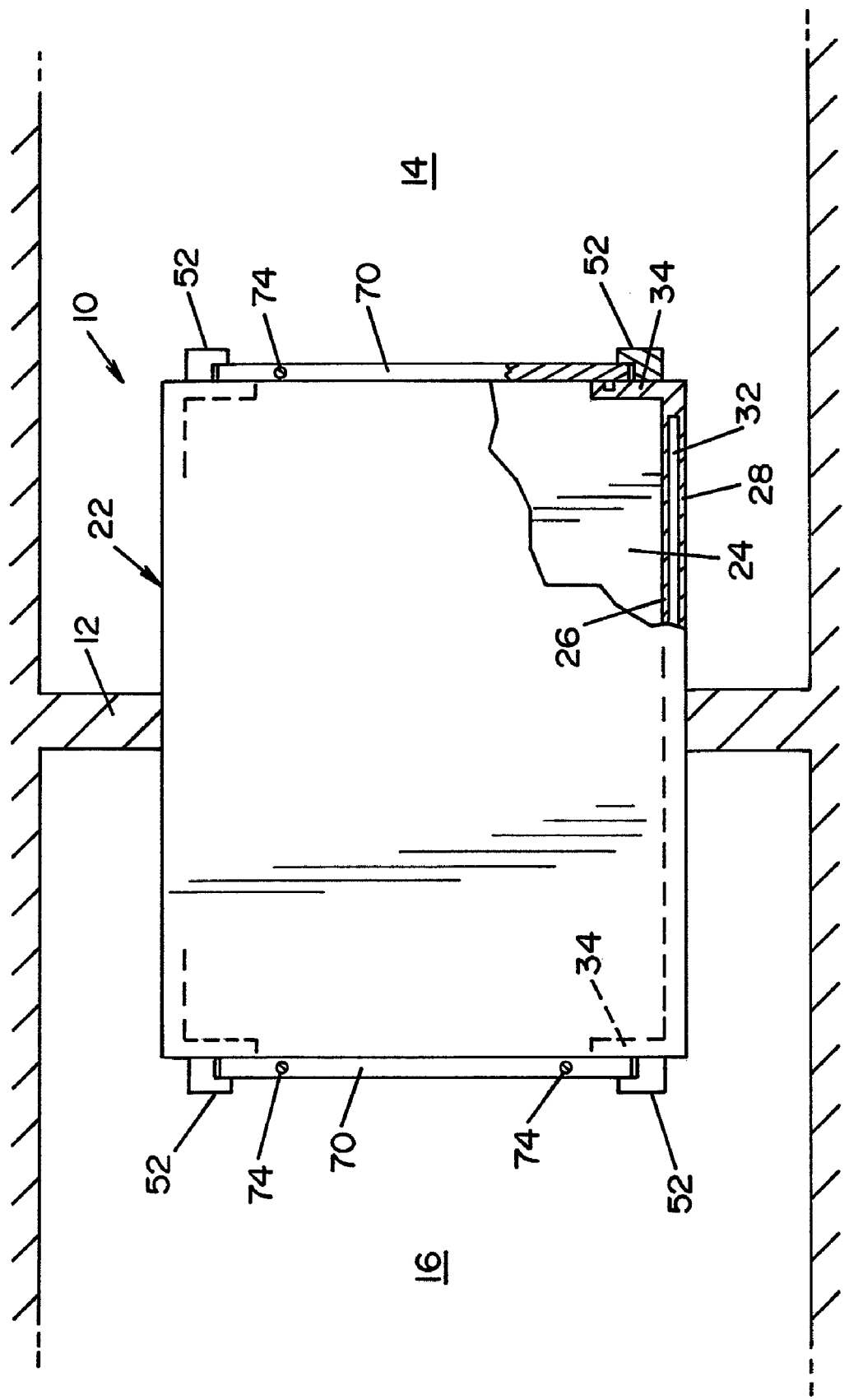
FIG. 1 is a partially-sectioned, top plan view of a steam sterilizer disposed within a wall that separates a "contaminated room" from a "clean room"

Referring now to the drawings wherein the showings are for the purpose of illustrating a preferred embodiment of the invention only and not for the purpose of limiting same, FIG. 1 shows a top plan view of a steam sterilizer 10. FIG. 1 is a partially sectioned, top plan view of steam sterilizer 10, showing steam sterilizer 10 disposed within a wall 12 that divides a "contaminated room" 14 from a "clean room" 16. As used herein, the term "contaminated room" refers to a room where contaminated articles or objects to be sterilized are located prior to sterilization. The term "clean room" refers to a room wherein articles or goods sterilized in sterilizer 10 may be removed for further handling following a sterilization cycle.

Sterilizer 10 is basically comprised of a body 22 defining an internal sterilization chamber 24. In the embodiment shown, sterilizer body 22 is generally rectangular in shape. Sterilizer body 22 is defined by an inner wall 26 and an outer wall 28. Outer wall 28 is spaced from inner wall 26 to define a cavity 32 surrounding sterilizer chamber 24. Cavity 32 is to be used as a steam jacket as shall be described in greater detail below. End plates 34 are attached to the distal ends of sterilizer body 22. In the embodiment shown, each end of sterilizer 10 is generally identical. Accordingly, only one end shall be described in detail, it being understood that such description applies to both ends of sterilizer 10.

Figure 2:
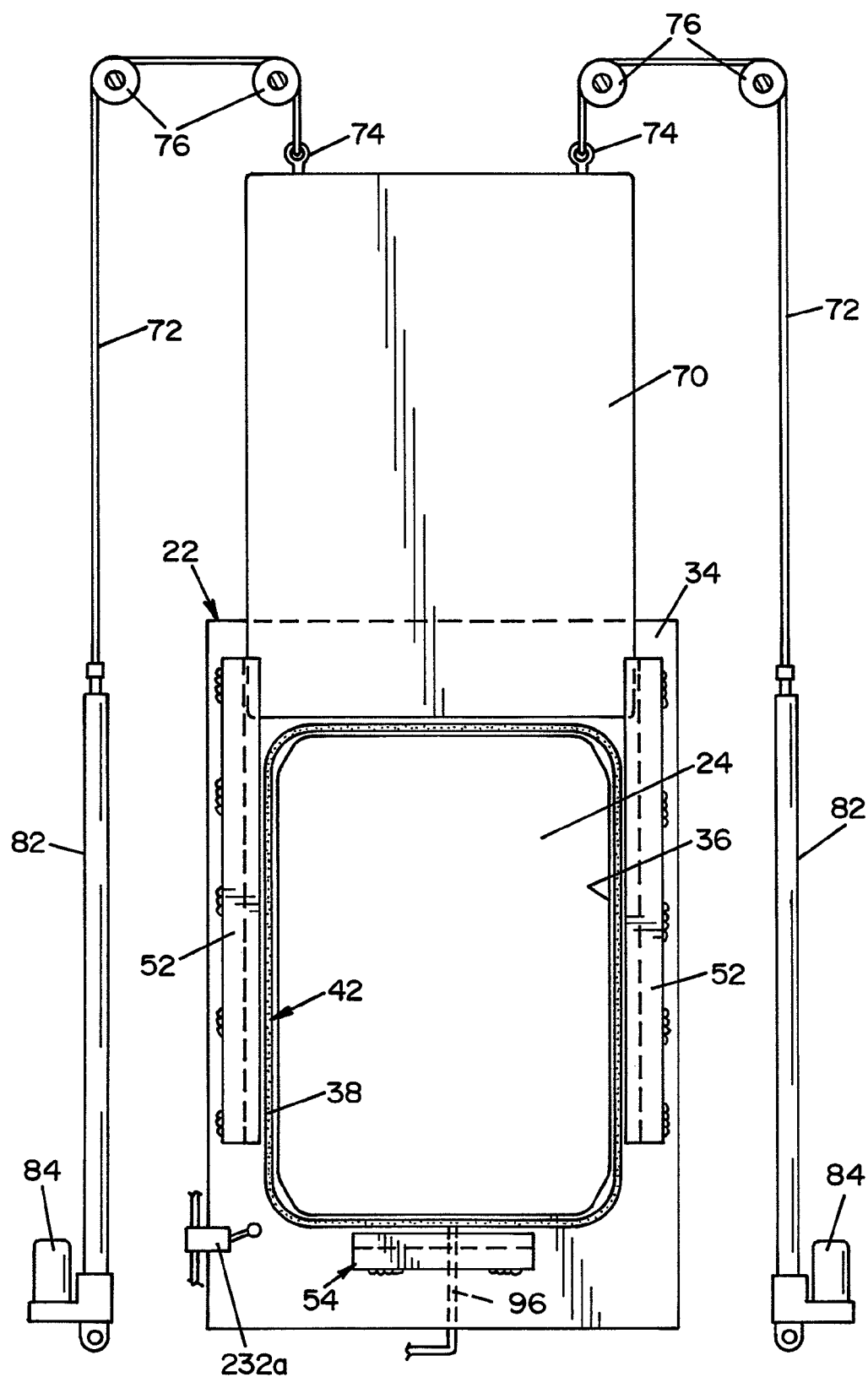
FIG. 2 is an enlarged, elevational view of one end of the steam sterilizer shown in FIG. 1, showing a door on a steam sterilizer in an open position.
Figure 4:
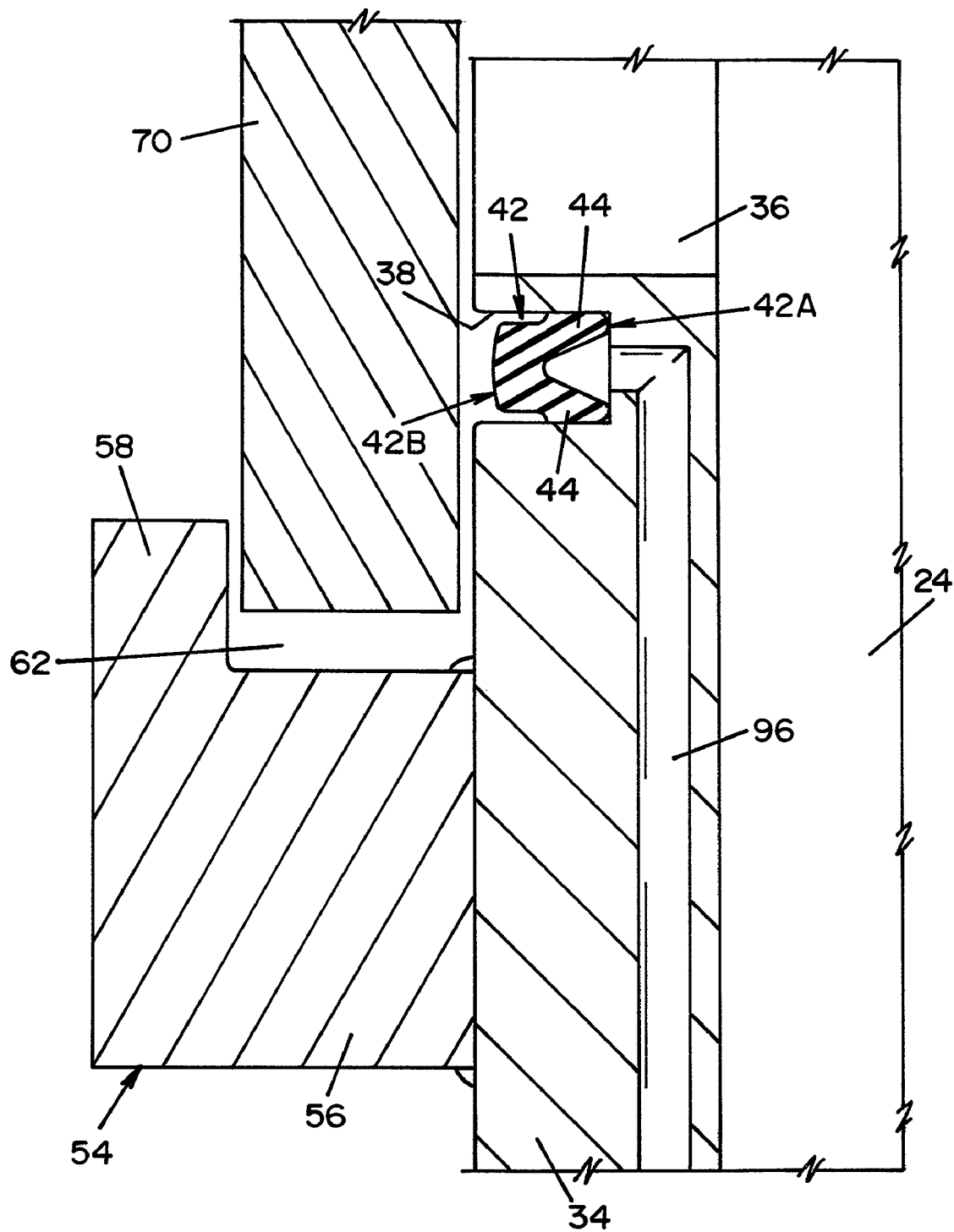
FIG. 4 is an enlarged, sectional view taken along lines 4-4 of FIG. 3, showing a seal assembly for forming a seal between a door and one end of a sterilizer chamber, the seal being shown in a non-sealing position.
Figure 5:
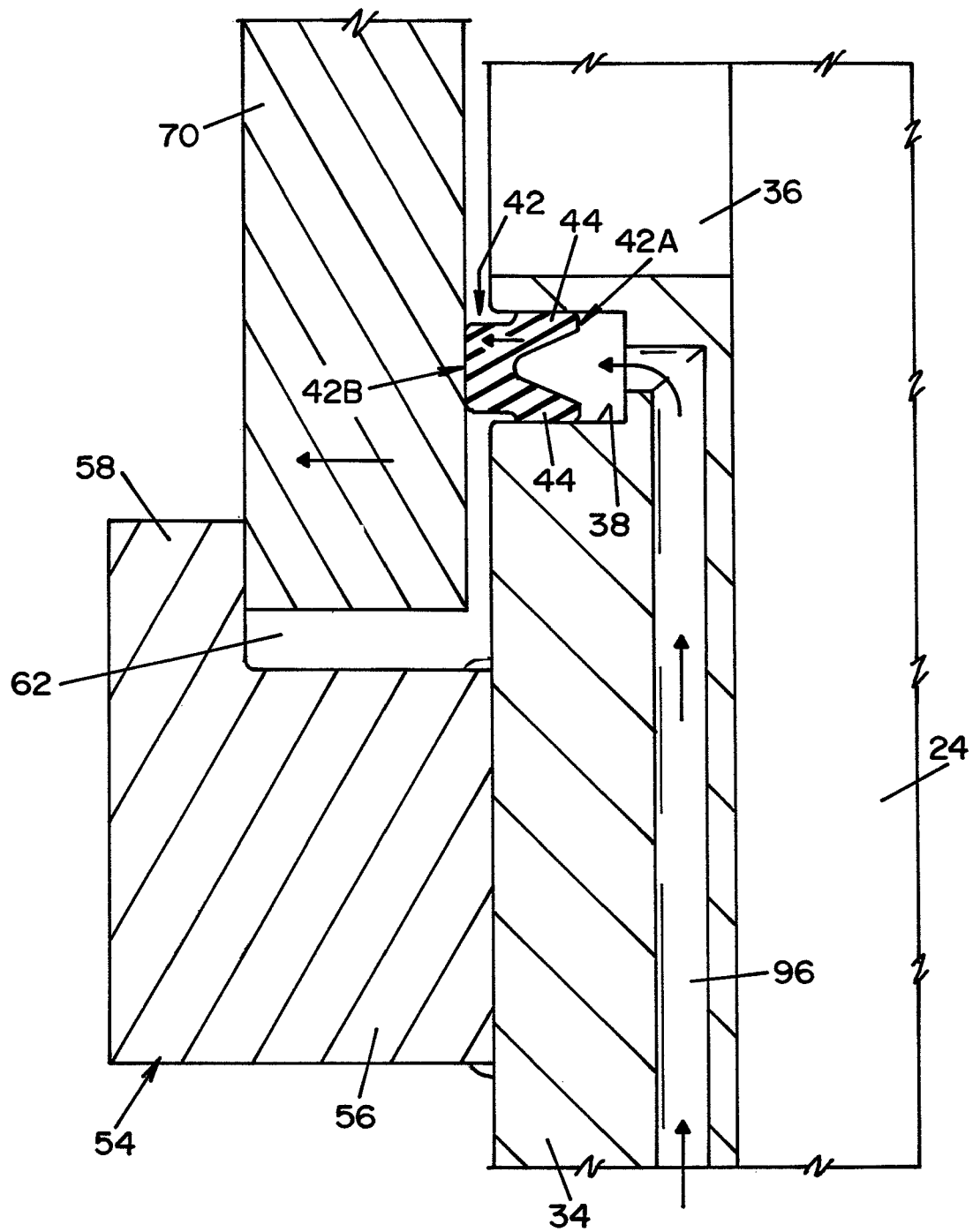
FIG. 5 is a view of the seal assembly shown in FIG. 4, showing the seal system in a door-sealing configuration.
Figure 6:
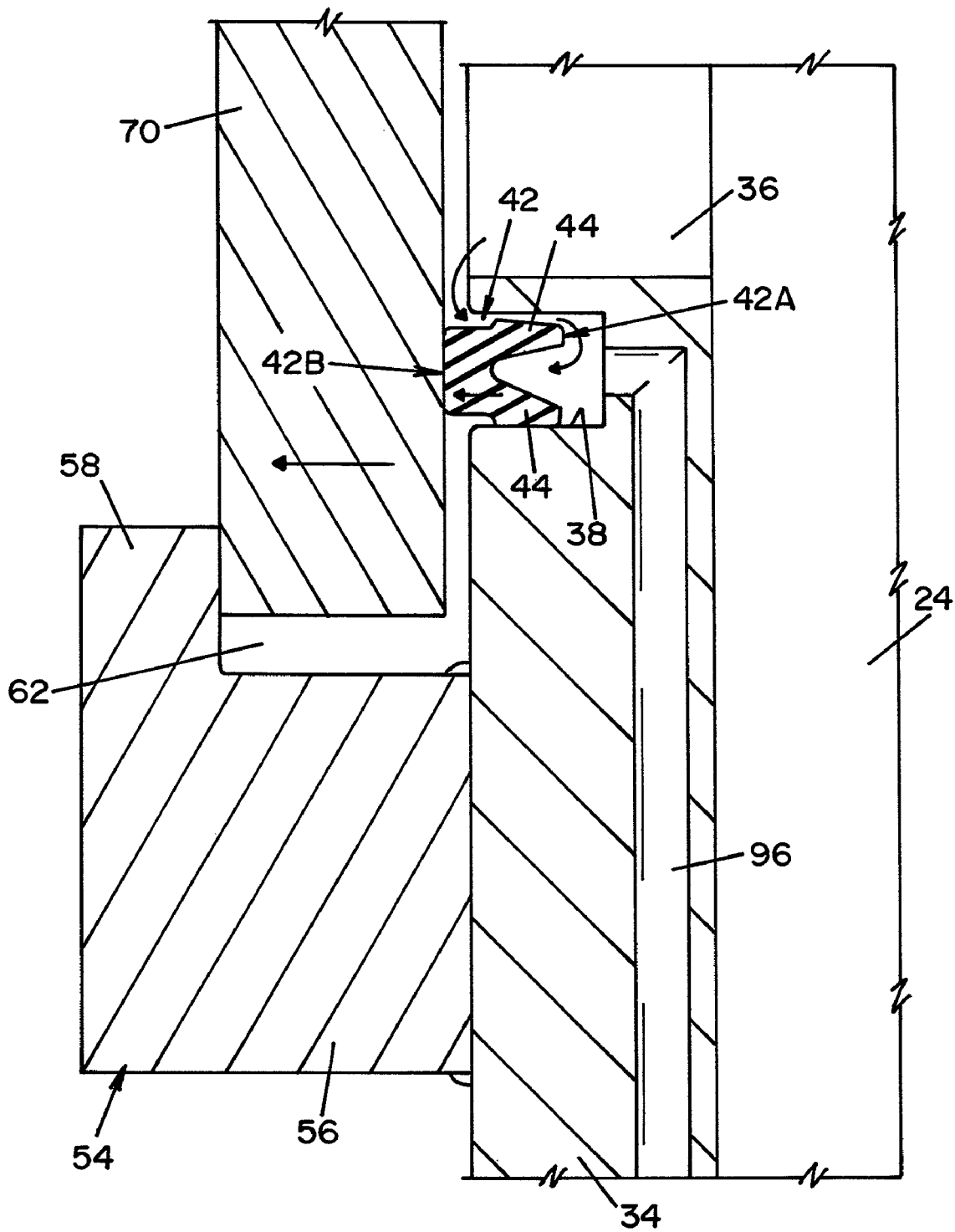
FIG. 6 is a sectional view of the door-seal system shown in FIGS. 4 and 5, showing the door-seal system in a door-sealing configuration and illustrating how pressure within the sterilizer chamber maintains a seal-forming condition during a utilities failure situation.

As best seen in FIG. 2, each end plate 34 is generally rectangular in shape and is attached to an end of sterilizer body 22. A rectangular opening 36 is formed at each end plate 34 to define an access opening to sterilization chamber 24 of sterilizer body 22. As best seen in FIGS. 4-6, a slot 38 is formed in the surface of end plate 34 to extend around the periphery of access opening 36. Slot 38 is dimensioned to receive a seal element 42 that shall be described in greater detail below. A lateral guide rail 52 is disposed along each lateral side of access opening 36, as best seen in FIG. 2. A door support 54 is disposed across the lower end of end plate 34. In the embodiment shown, the lateral guide rails 52 and door support 54 have similar cross-sections. Both are generally L-shaped in cross-section. In this respect, lateral guide rails 52 and door support 54 have a base portion 56 dimensioned to be attached to the outer surface of end plate 34 (See FIGS. 4 and 5). Each guide rail 52 and door support 54 includes a lip or ledge 58 extending to one side of base portion 56, as best illustrated in FIG. 4. Lateral guide rails 52 are disposed along end plate 34 to extend vertically, with lip or leg portion 58 of one guide rail 52, extending toward lip or leg portion 58 of the other guide rail 52. Door support 54 extends transversely across the base of end plate 34 below the bottom edge of access opening 36, as best seen in FIG. 2. Sterilizer body portion 22 and end plates 34 of steam sterilizer 10 are preferably formed of a non-reactive metal, such as stainless steel. Guide rails 52 and door support 54 are likewise formed of the same metal and are preferably attached to the outer facing surface of end plates 34 by welding. When attached to the outer surface of end plates 34, the lateral guide rails 52 basically form opposing slots 62 that extend vertically along the sides of access opening 36 (See FIG. 4). Slots 62 in lateral guide rails 52 are dimensioned to receive a door 70. In the embodiment shown, door 70 is comprised of a flat, rectangular plate dimensioned such that the lateral edges of door 70 slides within slots 62 defined by lateral guide rails 52 and the surface of end plate 34.

Figure 3:
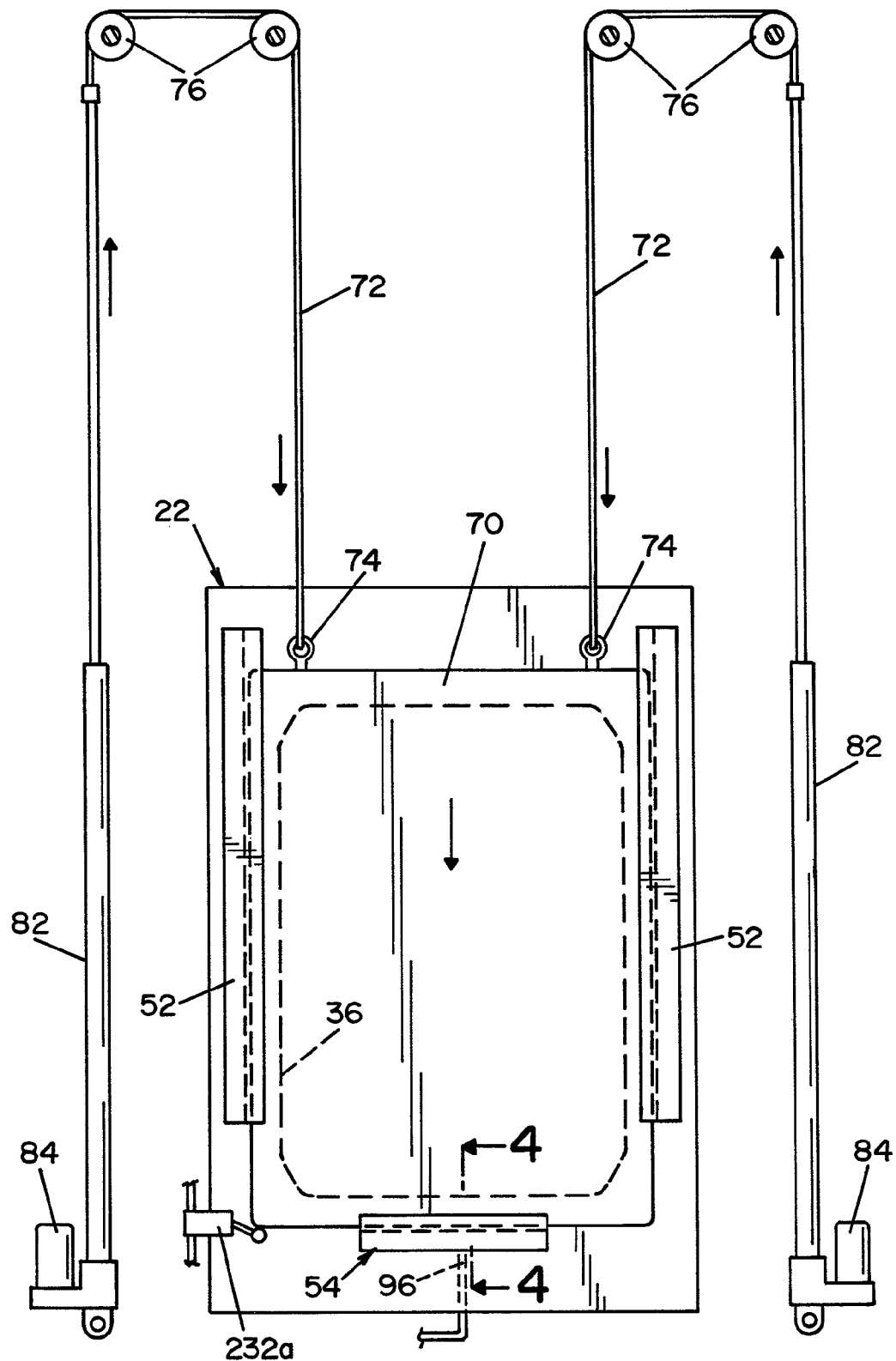
FIG. 3 is an elevational view of one end of the steam sterilizer shown in FIG. 1, showing a door on the steam sterilizer in a closed position.

Door 70 is supported by cables 72. One end of cables 72 is attached to eyelets 74 that, in turn, are attached to the upper edge of rectangular door 70. Cables 72 extend over a pair of pulleys 76, with the other end of cables 72 being attached to actuators 82 that are for moving door 70. Actuators 82 may be comprised of hydraulic or pneumatic cylinders. In the embodiment shown, actuators 82 are comprised of linear actuators driven by motors 84 mounted at the lower end of actuators 82. Actuators 82 are operable to move in unison to move rectangular door 70 between a first, open, position, as best seen in FIG. 2, wherein access to sterilization chamber 24 of sterilizer 10 is available, to a second, closed position, wherein door 70 is lowered by actuators 82 to a position, best seen in FIG. 3, where the lower edge of rectangular door 70 is supported by door support 54 that traverses end plates 34 below access opening 36. A valve 232a, shown in FIGS. 2 and 3, is provided near the lower end of access opening 36 to determine when door 70 is in a second, closed position, as shall be discussed in greater detail below.

Referring now to FIGS. 4, 5, and 6, seal element 42 is best seen. Seal element 42 is a one-piece endless element formed of an elastomeric material. Seal element 42 has a generally U-shaped cross-section, defining spaced-apart leg portions 44 along an inner portion 42A of seal element 42. An outer portion 42B of seal element 42 is slightly domed and is narrower in cross-section than the inner portion 42A. As shown in FIGS. 4-6, seal element 42 is disposed within slot 38 that surrounds access opening 36, with leg portions 44 of seal element 42 disposed in the bottom of slot 38. In this respect, domed outer portion 42B of seal element 42 faces door 70 when door 70 is in a closed position. As shown in FIGS. 4-6, a channel 96 is formed through the bottom of end plate 34 and communicates with the bottom of slot 38.

Figure 7:
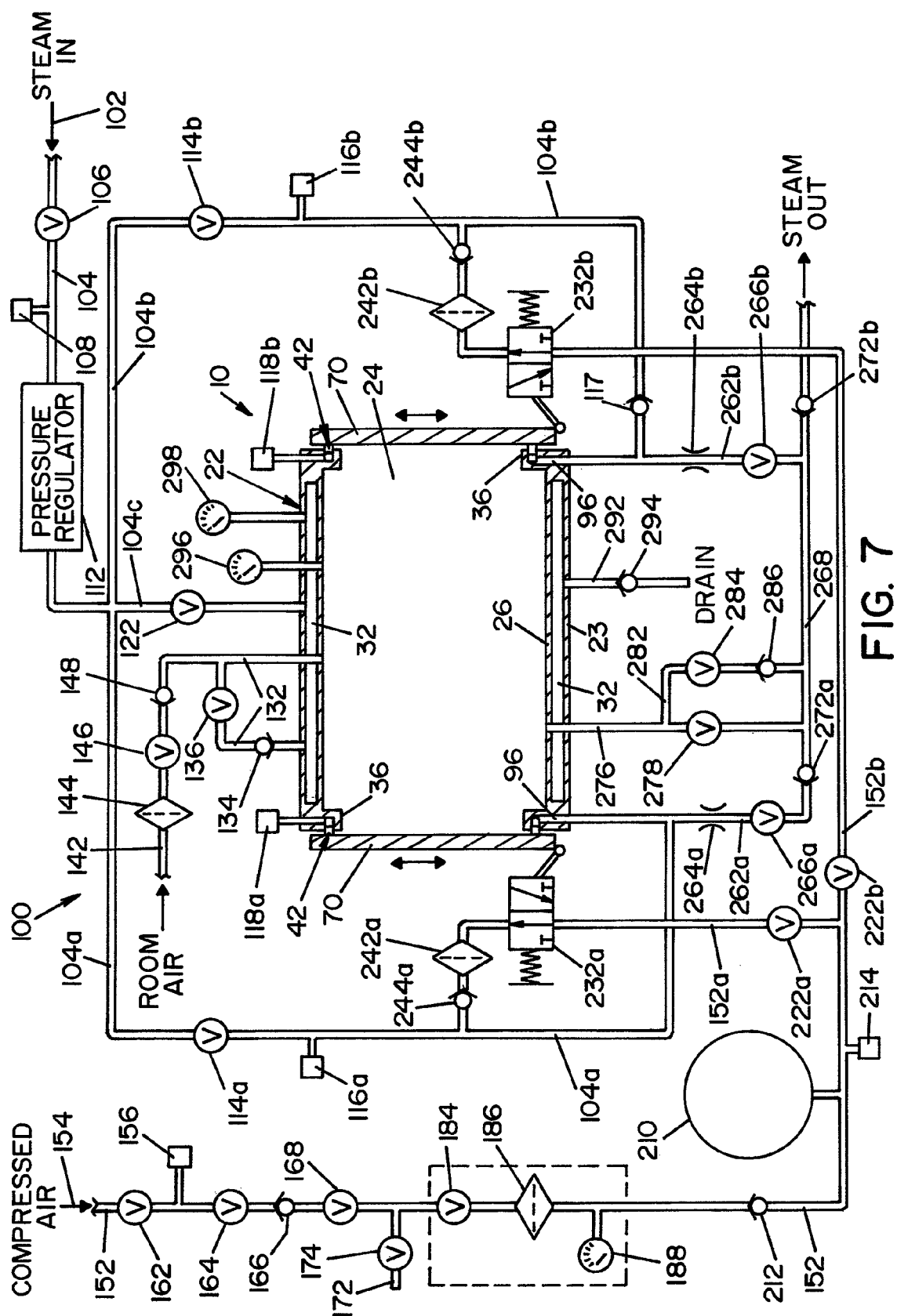
FIG. 7 is a schematic view of a door-sealing system for a steam sterilizer, illustrating a preferred embodiment of the present invention.

Referring now to FIG. 7, an operating system 100 for establishing a seal between door 70 and end plate 34 for maintaining the seal in the event of a utilities failure is shown.

A source 102 of pressurized steam communicates with steam sterilizer 10 through a main steam line 104. A control valve 106 is provided in main steam line 104 to control flow therethrough. A pressure switch 108 is provided in main steam line 104 downstream from control valve 106. Pressure switch 108 is set at a desired minimum pressure level to provide a signal to a system controller (not shown) that the pressure of the incoming steam is at or above the desired minimum pressure level. A pressure regulator 112 downstream of valve 106 and pressure switch 108 regulates the steam pressure to steam sterilizer 10 at a desired operating pressure. Downstream from pressure regulator 112, main steam line 104 branches off into three branch steam lines, designated 104a, 104b, and 104c. Branch steam lines 104a and 104b communicate respectively with passages 96 in end plates 34 of sterilizer 10. In this respect, branch steam lines 104a and 104b communicate with the inner side of seal elements 42 within slots 38 in end plates 34. Valves 114a, 114b are provided respectively in branch steam lines 104a and 104b to control the flow of steam therethrough. Pressure transducers 116a, 116b are disposed downstream of valve 114a, 114b, respectively. Pressure transducers 116a, 116b are connected to the system controller to provide an indication of the pressure that exists within branch steam lines 104*a* and 104*b*. A set of pressure switches 118*a*, 118*b* are provided to communicate with slots 38 in end plates 34. Pressure switches 118*a*, 118*b* provide an indication that a desired pressure exists on the inner side of seal elements 42, as shall be described in greater detail below. A directional check valve 117 is disposed in branch steam line 104*b* downstream from pressure switch 116*b*.

Branch steam line 104*c* is connected with cavity 32, defined by inner and outer walls 26, 28 of sterilizer body 22. A valve 122 disposed in branch steam line 104*c* controls the flow of steam therethrough.

A connecting line 132 connects cavity 32 of sterilizer body 22 to internal sterilization chamber 24. A directional check valve 134 is disposed in connecting line 132 to limit flow through connecting line 132 to steam flowing from cavity 32 to sterilization chamber 24. A valve 136 is also disposed in connecting line 132, downstream of check valve 134, to control flow through connecting line 132.

A vent line 142 is connected to connecting line 132, downstream of valve 136. Vent line 142 communicates with external air, as schematically illustrated in FIG. 7. A filter 144 is provided in vent line 142 to filter air flowing through vent line 142. A valve 146, downstream of filter 144, controls flow through vent line 142. A directional check valve 148 is also provided in vent line 142, downstream from valve 146, to limit air flow through vent line 142 to air flowing into sterilization chamber 24.

An air line 152 is provided to communicate with branch steam lines 104*a* and 104*b*. Air line 152 is connected to a source 154 of compressed air. Typically, the source of compressed air would be building utilities where steam sterilizer 10 is installed. A pressure switch 156 is provided in air line 152 to provide the system controller with a signal indicative of the incoming air pressure. Valves 162, 164 are provided in air line 152, on opposite sides of pressure switch 156, to enable isolation of pressure switch 156. A directional control valve 166 is provided downstream of pressure switch 156 and valve 164. The directional control valve 166 limits air flow through air line 152 to operating system 100. A valve 168 is disposed downstream of directional valve 166.

An auxiliary air inlet line 172 communicates with air line 152 downstream from valve 168. A valve 174 is disposed in auxiliary air line 172 to control flow therethrough. A valve 184 is also disposed downstream of auxiliary air inlet line 172. An air filter 186 and pressure gauge 188 are disposed downstream of auxiliary air inlet line 172 and valve 174.

A pressure storage tank 210 is disposed downstream of filter 186 and pressure gauge 188. A directional check valve 212 is disposed in air line 152 between pressure storage tank 210 and filter 186 and pressure gauge 188 to restrict air flow in air line 152 to an incoming direction.

A pressure transducer 214 is disposed relative to pressure storage tank 210 to provide the system controller with an indication of the pressure in storage tank 210.

Downstream from pressure storage tank 210, air line 152 branches into two branch air lines 152*a*, 152*b*. Valves 222*a*, 222*b* are disposed respectively in each of branch air lines 152*a*, 152*b*. Branch air lines 152*a*, 152*b* connect respectively to branch steam lines 104*a* and 104*b*.

Two position control valves 232*a*, 232*b* are disposed in branch air lines 152*a*, 152*b*, respectively. Each valve 232*a*, 232*b* has a first position, allowing flow through branch air lines 152*a*, 152*b*, and a second position obstructing flow through branch air lines 152*a*, 152*b*. As schematically illustrated in FIG. 7, control valves 232*a*, 232*b* are normally biased to the second position restricting flow through branch air lines 152*a*, 152*b*. Operation of control valves 232*a*, 232*b* is related to the position of doors 70. When doors 70 are in a closed position, control valves 232*a*, 232*b* are moved to the first position, allowing air through branch air lines 152*a*, 152*b*. When doors 70 are in an open position, control valves 232*a*, 232*b* are in a second position, obstructing the flow of air through branch air lines 152*a*, 152*b*. Between control valves 232*a*, 232*b* and the location where branch air lines 152*a*, 152*b* communicate with branch steam lines 104*a*, 104*b*, secondary air filters 242*a*, 242*b* are provided to filter air flowing through branch air lines 152*a*, 152*b*. Directional check valves 244*a*, 244*b* are disposed downstream of air filters 242*a*, 242*b* to prevent steam from branch steam lines 104*a*, 104*b* from flowing into branch air lines 152*a*, 152*b*.

Drain lines 262*a*, 262*b* are attached, respectively, to branch steam lines 104*a*, 104*b*. Flow restrictors 264*a*, 264*b* are provided in drain lines 262*a*, 262*b* to limit the flow of steam therethrough. Valves 266*a*, 266*b* are provided in drain lines 262*a*, 262*b* to control flow therethrough. Each drain line 262*a*, 262*b* is connected to a main drain line 268. Main drain line 268 is connected to a steam cooling system (not shown), wherein the steam is cooled by water for subsequent disposal. Such systems are conventionally known and, therefore, not described herein. Directional flow valves 272*a*, 272*b* are disposed in main drain line 268 downstream, respectively, from valves 266*a*, 266*b*.

A drain line 276 connects sterilization chamber 24 of sterilizer 10 to main drain line 268. A valve 278 disposed in drain line 276 controls the flow therethrough. An auxiliary drain line 282 branches off drain line 276. A second valve 284 in auxiliary drain line 282 controls flow therethrough. A check valve 286 is disposed in auxiliary drain line 282 between valve 284 and main drain line 268. A cavity drain line 292 is connected to cavity 32 in the steam jacket of sterilizer 10. A directional valve 294 is disposed within cavity drain line 292. Pressure gauges 296, 298 are provided to indicate pressure in sterilization chamber 24 and cavity 32, respectively.

Referring now to FIG. 7, the operation of sterilizer 10 and operating system 100 shall now be described. Operating system 100 is designed to be connected to building utilities that provide a source of steam and compressed air. More specifically, main steam line 104 is connected to a pressurized source of steam 102, and air line 152 is connected to a source of compressed air 154. Control valve 106 in main steam line 104 controls the flow of steam to operating system 100. In the embodiment shown, control valve 106 is a manual valve maintained in a normally open position. A pressure switch 108 is set to provide a signal to the system controller (not shown) should the pressure of the steam supplied to operating system 100 fall below a desired operating steam pressure. Pressure regulator 112 regulates the pressure of the incoming steam to a desired system operating pressure. Valve 162 in air line 152 controls the flow of compressed air to the operating system 100. Control valve 162 is preferably a manual valve maintained in an open position. Pressure switch 156 provides a signal to the system controller in the event that the air pressure supplied to operating system 100 falls below a desired air pressure.

In the embodiment shown, sterilizer 10 is disposed between a dirty room and a clean room. With such an arrangement, one door 70 would typically be in an open position to load or discharge articles from the sterilization chamber 24, while the other door 70 would be in a closed position. When a sterilization cycle is initiated, typically following loading of sterilization chamber 24 from the dirty-room side of sterilizer 10, door 70 to the contaminated room 14 would move to a closed position. As illustrated in FIG. 7, valves 232*a*, 232*b* are actuated whenever a door 70 is in a closed position. When in a closed position, valves 232a, 232b allow air line 152a to communicate with branch steam line 104a and allow branch air line 152b to communicate with branch air line 104b. When either door 70 is in an open position, the spring-biased valves 232a, 232b are moved to a blocking position, wherein branch air lines 152a, 152b do not communicate with branch air lines 104a, 104b.

With the doors 70 of sterilizer 10 in a closed position and valves 232a, 232b moved to a position as described above, the system controller undergoes a diagnostic routine to check proper functioning of system components.

During the diagnostic routine, the pressure in pressure storage tank 210 is checked. In this respect, according to the present invention, pressure storage tank 210 is provided to hold a predetermined volume of compressed air at a predetermined pressure. The volume of compressed air and the pressure of such air are sufficient to provide for back-up pressure to seal elements 42 in the event of system failure, as shall be described in greater detail below. To this end, prior to running a sterilization cycle, compressed air from compressed air source 154 is used to fill pressure storage tank 210. As indicated above, pressure storage tank 210 is preferably filled to a predetermined pressure. In this respect, valve 168 in main air line 152 is a pressure-controlled valve that is operable only when a predetermined threshold pressure is sensed in air line 152. Once such threshold pressure has been reached, compressed air is allowed to flow through main air line 152 to pressure storage tank 210. The incoming air is filtered by filter 186 and regulated by valve 184 to insure the desired pressure is stored in tank 210. In this respect, as will be appreciated, pressure regulating valve 184 is set below pressure control valve 168.

Control valves 222a and 222b in branch air lines 152a, 152b, respectively, are in a closed position wherein pressure storage tank 210 is isolated from the rest of operating control system 100. Control valves 222a, 222b are normally open valves that are maintained in a closed position by the system controller. Pressure transducer 214 provides a signal to the system controller that corresponds to the pressure within pressure storage tank 210. Directional check valve 212 in main air line 152 maintains the pressure in pressure storage tank 210 in the event that the pressure of incoming air from source 154 should drop below the desired storage pressure for the compressed air in pressure storage tank 210. The system controller, by monitoring pressure transducer 214 when various valves within system 100 are closed, can determine the integrity of system 100 in the vicinity of pressure storage tank 210, and can also calculate remaining compressed air reserve time, as shall be described in greater detail below. The controller also checks the integrity of door seal elements 42 based on signals from transducers 116a and 116b. If signals from pressure transducers 116a, 116b indicate that a seal element 42 has failed the leak test, the controller will warn the operator that a leak has been detected.

When a sterilization cycle is initiated, the system controller determines if the pressure in pressure storage tank 210 is at a desired level. The system also determines if the leak rate within operating system 100 is below an acceptable level. If pressure in pressure tank 210 is at the desired level and the leak rate is below an acceptable level, a sterilization cycle is allowed to begin by the system controller opening valves 114a, 114b in branch steam lines 104a, 104b to allow steam to flow into slots 38 in end plates 34. The pressurized steam on the inner portions of slot 38 forces seal elements 42 into engagement with the inner surface of doors 70, thereby forming a seal between the inner surface of each door 70 and the outer surface of each end plate 34. Pressure switches 118a, 118b, that communicate with slots 38, are operable to provide a signal to the system controller, i.e., in the event that the steam pressure to the underside of seal elements 42 falls below a necessary operating seal pressure.

Valve 122 is normally in an opened position to allow steam into cavity 32 between inner wall 26 and outer wall 28 of sterilizer body 22, when sterilizer 10 is powered up. Cavity 32 acts as a warming jacket for sterilizer body 22. Once a seal is established between door 70 and sterilizer body 22, valve 136 in connecting line 132 is opened to allow steam from cavity 32 to flow into sterilizer chamber 24. Directional check valve 134 in connecting line 132 allows flow from cavity 32 into sterilizer chamber 24, but prevents flow in the opposite direction.

In addition, check valve 148 in vent line 132 prevents steam from flowing out of system 100 into vent line 142. In addition, during this portion of a sterilization cycle, valve 146 is in the closed position, further preventing flow through vent line 142.

As will be appreciated, valves 266a, 266b, 278 and 284 in drain lines 262a, 262b, 276, and 282 are in a closed position, preventing steam from exiting from sterilization chamber 24 or from slots 38 in end plates 34. Valves 278 and 284 may be opened during the cycle to drain steam from sterilization chamber 24, as needed by the system controller. The pressurized steam within sterilization chamber 24 is maintained for a predetermined period of time sufficient to sterilize articles within sterilization chamber 24.

Throughout the sterilization process, the pressure switches and pressure sensors of system 100 monitor the operating conditions of sterilizer 10 to insure proper functioning thereof. Once a sterilization cycle is complete, steam within chamber 24 is released by opening valve 278, which allows steam to flow from chamber 24 through line 268 to a cooling unit (not shown) that turns the steam to water, as is conventionally known. Valve 266a, 266b remain closed, as steam is drained from chamber 24, to maintain steam pressure to seal elements 42. Filtered air is allowed into chamber 24 through vent line 142 by opening valve 146. Valve 266a that is associated with the clean side 16, is opened at the end of the cycle and a vacuum is applied to move seal element 42 away from door 70 before door 70 is opened. The system controller then actuates actuators 82 to move door 70 in clean room 16 to an opened position. With door 70 in clean room 16 in an opened position, sterilized articles may be removed from sterilization chamber 24. The system controller prevents cross-contamination by keeping door 70 in contaminated room 14 closed while door 70 in clean room 16 is open. Still further, check valve 272a in drain line 152b prevents contaminants from drain line 152b from entering system 100. Similarly, valve 117 in branch steam line 104b prevents contaminants from contaminated room 14 from entering system 100.

In accordance with one aspect of the present invention, the compressed air in pressurized storage tank 210 provides back-up pressure to seal elements 42 in the event of a failure in either the steam utility and/or the air utility to system 100. In this respect, valves 222a, 222b are opened to allow pressurized air from storage tank 210 to flow through branch air lines 152a, 152b and communicate with branch steam lines 104a, 104b that, in turn, connect to the slots 38 in end plates 34. The pressure in pressure storage tank 210 provides pressure to maintain the seal for a predetermined period of time. In one embodiment of the present invention, pressure storage tank 210 is designed to maintain seal elements 42 in sealing engagement with doors 70 for at least eight (8) hours.

Should the back-up air pressure from air pressure storage tank 210 continue to deteriorate, according to another aspect of the present invention, the steam pressure within sterilization chamber 24 is used to maintain an active seal independent of the air and steam sources. In this respect, the leg portion 44 of seal element 42 that is adjacent sterilization chamber 24 is under a higher pressure than the leg portion 44 of seal element 42 that is exposed to the outside environment.

As best seen in FIG. 6, as pressure within slots 38 (behind seal element 42) decreases, it will eventually reach a level where the pressure in slots 38 is below the pressure within sterilization chamber 24. As will be appreciated, even at this pressure, the pressure exerted against seal element 42 is still greater than outside atmospheric pressure. As a result, the higher pressure within sterilization chamber 24 causes the leg portion 44 that is adjacent sterilization chamber 24 to move away from the side of slot 38, allowing pressure within sterilization chamber 24 to be used to maintain the outer face of seal element 42 in engagement with door 70 and the other leg portion 44 of seal element 42 in engagement with the side of slot 38. In other words, the pressure within sterilization chamber 24 further provides pressure to maintain a seal between doors 70 and end plates 34.

In accordance with another aspect of the present invention, auxiliary air line 172 provides an additional means of providing back-up air pressure to seal elements 42. In this respect, auxiliary pressurized air tanks may be connected to auxiliary air line 172. Valve 174, which is normally closed, may be opened to allow pressurized air into air line 152 to communicate to branch air lines 152a, 152b to auxiliary steam lines 104a, 104b, respectively, and, in turn, to pressurized seal elements 42 in slots 38.

The present invention thus provides an operating system for a steam sterilizer 10 that provides back-up air pressure to maintain a seal between doors 70 of sterilizer 10 and end plates 34 of sterilizer 10 in the event of system failures. Still further, the design of seal elements 42 allows steam pressure of the sterilizing steam within the sterilizing chamber 24 to also be used to prolong the door seal, in a manner as described above. Still further, system 100 provides means for connecting auxiliary storage tanks to the air back-up system to further provide extended seal engagement during a system failure.

The present invention thus provides an active seal system with an air back-up system that maintains the doors and sealing engagement with the sterilizer body, despite system failure.

In accordance with another aspect of the present invention, a back-up power pack is provided on the control system to provide electrical power in the event that utility electrical power is lost to the sterilizer. In the event of electrical power loss to sterilizer 10, the control automatically switches to the battery which is designed to power the control for at least eight (8) hours. The system further includes an alarm if a failure is detected within the back-up battery.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. In a sterilizer having,
a housing defining a sterilization chamber, an opening in said housing communicating with said chamber, a surface surrounding said opening and a door movable between one of an open position allowing access to said chamber through said opening and a closed position covering said opening, the improvement, comprising:
a seal element associated with said surface for forming a fluid-tight seal between said door and said surface when said door is in said closed position;
an operating system connectable to a first source of pressure for applying pressure to one side of said seal from said first source of pressure to force said seal into engagement with said door, said operating system including a vessel containing a compressed gas that is connectable to said one side of said seal and a conduit connected to said one side of said seal element;
sensing means for monitoring the pressure applied to said seal from said first pressure source; and
first and second valve means for selectively connecting said conduit to said first source of pressure and to said vessel wherein said first valve means disconnects said first source of pressure from said conduit and said second valve means connects said compressed gas in said vessel to said conduit if said sensing means detects a pressure from said first source of pressure below a set pressure sufficient to sustain a seal between said door and said surface.

2. A sterilizer as defined in claim 1, wherein said compressed gas in said vessel is air.

3. A sterilizer as defined in claim 1, wherein said seal element is generally U-shaped and has an upper end and a lower end defined by two spaced-apart leg portions.

4. A sterilizer as defined in claim 3, wherein said seal element is disposed in a slot in said surface, said seal element oriented in said slot with said leg portions disposed in the bottom of said slot wherein one of said leg portions engages one side of said slot and another of said leg portions engages another side of said slot.

5. A sterilizer as defined in claim 4, wherein said leg portion adjacent to said sterilization chamber moves to a position spaced away from said side of said slot for allowing said one side of said seal element to be in communication with said sterilization chamber when a pressure in said sterilization chamber is greater than a pressure on said one side of said seal element.

6. A sterilizer as defined in claim 1, further comprising
second sensing means for monitoring the pressure applied to said seal from said vessel; and
third valve means for connecting an auxiliary pressure supply to said conduit, if both said pressure from said first source of pressure and said pressure from said vessel falls below a set operating pressure.

* * * * *